(12) United States Patent
Bowers, III et al.

(10) Patent No.: US 9,791,422 B2
(45) Date of Patent: Oct. 17, 2017

(54) ANALYSIS OF PERIODIC INFORMATION IN A SIGNAL

(71) Applicant: CSI Technology, Inc., Wilmington, DE (US)

(72) Inventors: Stewart V. Bowers, III, Knoxville, TN (US); Robert D. Skeirik, Knoxville, TN (US)

(73) Assignee: Computational Systems, Inc., Knoxville, TN (US)

( * ) Notice: Subject to any disclaimer, the term of this patent is extended or adjusted under 35 U.S.C. 154(b) by 613 days.

(21) Appl. No.: 14/316,883

(22) Filed: Jun. 27, 2014

(65) Prior Publication Data

US 2015/0012247 A1   Jan. 8, 2015

Related U.S. Application Data

(60) Provisional application No. 61/842,035, filed on Jul. 2, 2013.

(51) Int. Cl.
| | |
|---|---|
| *G01H 1/00* | (2006.01) |
| *G01N 29/46* | (2006.01) |
| *G01N 29/44* | (2006.01) |
| *G01N 29/50* | (2006.01) |

(52) U.S. Cl.
CPC .............. *G01N 29/46* (2013.01); *G01H 1/00* (2013.01); *G01N 29/4427* (2013.01); *G01N 29/4454* (2013.01); *G01N 29/50* (2013.01)

(58) Field of Classification Search
CPC ..................................................... G01H 1/00
USPC ......................................................... 702/189
See application file for complete search history.

(56) References Cited

U.S. PATENT DOCUMENTS

| | | | |
|---|---|---|---|
| 5,895,857 | A  |  4/1999 | Robinson et al. |
| 5,943,634 | A  |  8/1999 | Piety et al. |
| 6,408,696 | B1 |  6/2002 | Jong |
| 6,651,012 | B1 | 11/2003 | Bechhoefer |
| 7,010,445 | B2 |  3/2006 | Battenberg et al. |
| 7,133,801 | B2 | 11/2006 | Song |
| 7,136,794 | B1 | 11/2006 | Bechhoefer |
| 7,194,383 | B2 |  3/2007 | Clarke et al. |

(Continued)

FOREIGN PATENT DOCUMENTS

| | | |
|---|---|---|
| EP | 1097363 B1   | 12/2007 |
| WO | 2012172369 A2 | 12/2012 |

*Primary Examiner* — Bryan Bui
(74) *Attorney, Agent, or Firm* — Luedeka Neely Group, P.C.

(57) ABSTRACT

A "periodic signal parameter" (PSP) indicates periodic patterns in an autocorrelated vibration waveform and potential faults in a monitored machine. The PSP is calculated based on statistical measures derived from an autocorrelation waveform and characteristics of an associated vibration waveform. The PSP provides an indication of periodicity and a generalization of potential fault, whereas characteristics of the associated waveform indicate severity. A "periodic information plot" (PIP) is derived from a vibration signal processed using two analysis techniques to produce two X-Y graphs of the signal data that share a common X-axis. The PIP is created by correlating the Y-values on the two graphs based on the corresponding X-value. The amplitudes of Y-values in the PIP is derived from the two source graphs by multiplication, taking a ratio, averaging, or keeping the maximum value.

9 Claims, 11 Drawing Sheets

(56) References Cited

U.S. PATENT DOCUMENTS 8,174,402 B2* 5/2012 Bouse ................ G05B 19/4065
340/635
2011/0098968 A1 4/2011 Srinivasa et al.

* cited by examiner

PSP = 0.05

PSP = 0.10

PSP = 0.115

PSP = 0.147

PSP = 0.52

ANALYSIS OF PERIODIC INFORMATION IN A SIGNAL

RELATED APPLICATIONS

This application claims priority to U.S. provisional patent application Ser. No. 61/842,035 filed Jul. 2, 2013, titled "Periodic Signal Parameter."

FIELD

This invention relates to analysis of signals. More particularly, this invention relates to methods for extracting periodic information from a vibration waveform or other signal containing periodic information.

BACKGROUND

By some estimates, up to half of all mechanical failures in process plants are induced by process conditions. Therefore, providing feedback to an operator that the process machines are being operated in a non-optimal configuration provides a way for the operator to avoid harmful operating states, thereby substantially extending mean time between failures (MTBF) or mean time between repairs (MTBR) on production assets.

Vibration analysis is a well proven technology for detecting faults in rotating machinery. The process of determining the severity and specifics of a fault can be very involved. Part of the analysis process involves determining whether periodic signals are present. While maintenance personnel are concerned with detailed analyses of faults, operations personnel only want to know if a problem exists. Providing a few fault-related parameters to the operator can be sufficient in accomplishing this task. Fault-related parameters can be related to amplitudes of energy from particular vibration frequencies (bandwidth), signal processing techniques such as PeakVue™, and the presence of periodic signals. Parameters calculated from bandwidth and signal processing techniques are well defined. However, a parameter indicating the presence of periodic signals has not been defined.

Further, the ability to detect mechanical faults in industrial machinery is a task requiring skilled analytical personnel with years of training and experience. Because of budgetary and personnel constraints, a qualified analyst may be pressed to analyze most or all of the equipment in a plant. Any technology, technique or tool that can simplify the analyst's job is valuable. Although the Fast Fourier Transform (FFT) is a technique that may be used to simplify the analyst's job, identifying important peaks in an FFT plot can be difficult due to low amplitude and noise issues. The analysis could be made easier with the derivation of a graph that reflects only periodic signals present in the measurement.

What is needed, therefore, is a system for calculating a periodic signal parameter based on an autocorrelation waveform derived form a vibration waveform. Those skilled in the art will see that autocorrelation is one of several ways to quantify the periodicity in a given signal. What is also needed is a system for deriving a graph, also referred to herein as a "periodic information plot," that reflects only periodic signals present in a measurement waveform.

SUMMARY

Periodic Signal Parameter

The autocorrelation coefficient function is a mathematical process that determines how much of the energy in a waveform is periodic. The pattern of the periodic peaks can be very helpful in identifying fault types. Recognizing these patterns and how to apply them requires an experienced analyst. Preferred embodiments of the present invention calculate a value that is representative of general periodic patterns, which in turn signify potential faults. This value, referred to herein as a "periodic signal parameter" (PSP), is calculated based on statistical measures derived from an autocorrelation waveform along with characteristics of the associated vibration waveform. While the PSP derived from the autocorrelation function produces an indication of periodicity and a generalization of potential fault, characteristics of the associated vibration waveform afford a measure of severity. The combination of these two identities provide further indication as to potential problems associated with machines on the plant floor. This is a significant advantage for a machine operator on the plant floor who may have little-to-no vibration analysis experience.

The process of calculating the PSP begins with taking the autocorrelation of a vibration waveform. Once this is accomplished, several statistical calculations are performed. In a preferred embodiment, these statistical calculations include the maximum absolute waveform peak, standard deviation of the waveform, maximum absolute peak after the first 3% of the waveform, crest factor of both the waveform and positive waveform values, and a sorted mean of positive waveform peak values. The sorted mean is preferably calculated from a subset of values, in this case the larger set is the positive waveform peak values. The sorted subset preferably comprises all peak values from the positive waveform, excluding outliers. The outliers are peak values that exceed a statistically defined standard deviation about the mean. Therefore, the sorted mean is the mean value of the sorted positive waveform peak subset.

Once the PSP is calculated, the peak-to-peak amplitude of the initial vibration waveform (the peak amplitude in the PeakVue™ waveform) is evaluated. Various aspects of the PeakVue™ process are described in U.S. Pat. No. 5,895,857 (Robinson et al.), U.S. Pat. No. 6,192,325 (Piety et al.), U.S. Pat. No. 6,549,869 (Piety et al.), U.S. Pat. No. 6,889,553 (Robinson et al.), U.S. Pat. No. 7,561,200 (Garvey et al.), U.S. Pat. No. 7,424,403 (Robinson et al.), U.S. Pat. No. 8,174,402 (Reeves et al.), 2014/0039833 (White et al.), and 2012/0041695 (Baldwin et al.), the entire contents of which are incorporated herein by reference. If the peak-to-peak amplitude of the associated vibration waveform exceeds predefined alarm limits, indication of particular faults are triggered based on the PSP value.

Because the autocorrelation of a waveform is normalized to ±1, the maximum standard deviation of the waveform is 1. Therefore, the base value of the PSP ranges from 0 to 1. Mathematical operations can be performed on the base value to achieve a desired scaling. An example would be to multiply the base value by 10 to achieve a PSP range from 0 to 10. Additionally, taking the square root of the PSP base value will accentuate variations in the lower end of the scale, which can then be multiplied by 10 to achieve a PSP range from 0 to 10. As discussed in more detail hereinafter, the PSP is calculated based on the value of the standard deviation of the autocorrelated waveform plus contributions centered on empirical observations from the other calculated statistical parameters mentioned above. Examples of autocorrelated waveforms along with the associated PSP values are provided in the detailed description.

The PSP may apply to autocorrelated waveforms derived from filtered and unfiltered acceleration, velocity or displacement waveforms as well as processed waveforms. Two examples of processed waveforms are results of the Peak-Vue™ signal processing and demodulation techniques.

Periodic Information Plot

As discussed above, the autocorrelation coefficient function is a mathematical process that indicates whether there is periodicity in a signal. When viewing an autocorrelation waveform, periodic signals are typically evident in the data. However, it is not easy to distinguish the exact frequency or amplitude of these periodic signals from the autocorrelation waveform. By taking a Fast Fourier Transform (FFT) of the autocorrelation waveform, distinct frequency values are evident. By comparing the autocorrelation spectrum to the standard spectrum, the true amplitude of each signal at these frequencies can be obtained.

Preferred embodiments described herein provide a method for analyzing and displaying data to reveal periodicity in a signal. The embodiments include processing the raw signal using two different sets of analysis techniques, thereby producing two X-Y graphic representations of the signal data that share a common X-axis. A third graph is created by correlating the Y-values on the first two graphs based on the corresponding X-value. The amplitude of each Y-value can be derived from the two source graphs using a variety of techniques, including multiplication, taking a ratio, averaging, or keeping the maximum value. The resulting synthesized graph, also referred to herein as a Periodic Information Plot (PIP), accentuates signal components that are pertinent to a given diagnosis while eliminating other undesired signal components. This provides for visualizing the data in a way that simplifies the recognition and quantification of desired characteristics present in the raw signal. The diagnosis may be accomplished either by a human or a computerized expert system. For a human analyst, the technique reduces training requirements while bringing increased efficiency and accuracy. With a computerized expert system, the technique provides new methods for diagnostic software to recognize significant patterns contained in the original signal.

Thus, the analysis process is made easier by providing the analyst with a spectrum showing only the periodic signals present in the data. While the same periodic information is present in the original spectrum generated from the original data, it is often difficult to recognize the periodic information because the noise levels are similar in magnitude to the periodic information.

BRIEF DESCRIPTION OF THE DRAWINGS

Further advantages of the invention are apparent by reference to the detailed description in conjunction with the figures, wherein elements are not to scale so as to more clearly show the details, wherein like reference numbers indicate like elements throughout the several views, and wherein.

DETAILED DESCRIPTION

Figure 1:
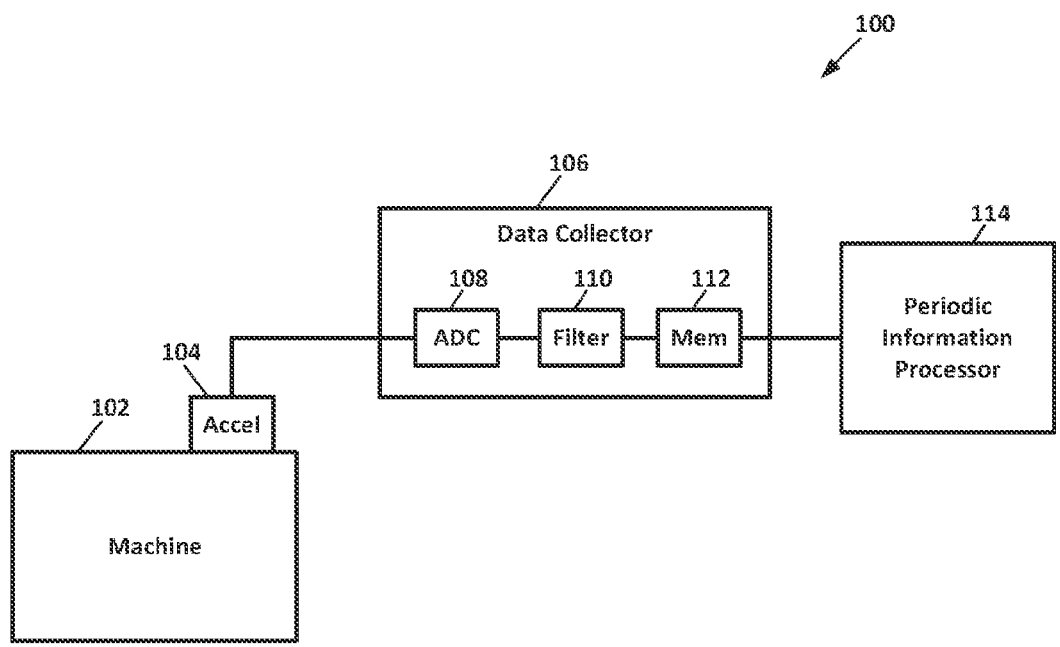
FIG. 1 depicts a functional block diagram of a system for deriving and analyzing periodic information in a signal according to a preferred embodiment of the invention.

FIG. 1 depicts an exemplary system 100 for deriving and analyzing periodic information in a vibration signal. In the embodiment of FIG. 1, a sensor 104, such as an accelerometer, is attached to a machine 102 to monitor its vibration. Although an accelerometer is depicted in the exemplary embodiment of FIG. 1, it should be appreciated that other types of sensors could be used, such as a velocity sensor, a displacement probe, an ultrasonic sensor, or a pressure sensor. The sensor 104 generates a vibration signal (or other type of signal for a sensor other than an accelerometer) that contains periodic information. The vibration signal is provided to a data collector 106 preferably comprising an analog-to-digital converter (ADC) 108 for sampling the vibration signal, a low-pass anti-aliasing filter 110 (or other type of filter), and buffer memory 112. For example, the data collector 106 may be a digital data recorder manufactured by TEAC or a vibration data collector. In the embodiment of FIG. 1, the vibration signal data is transferred from the data collector 106 to a periodic information processor 114 that performs the information processing tasks described herein. In an alternative embodiment, the processing tasks are performed by a processor in the data collector 106.

Periodic Signal Parameter

Figure 2:
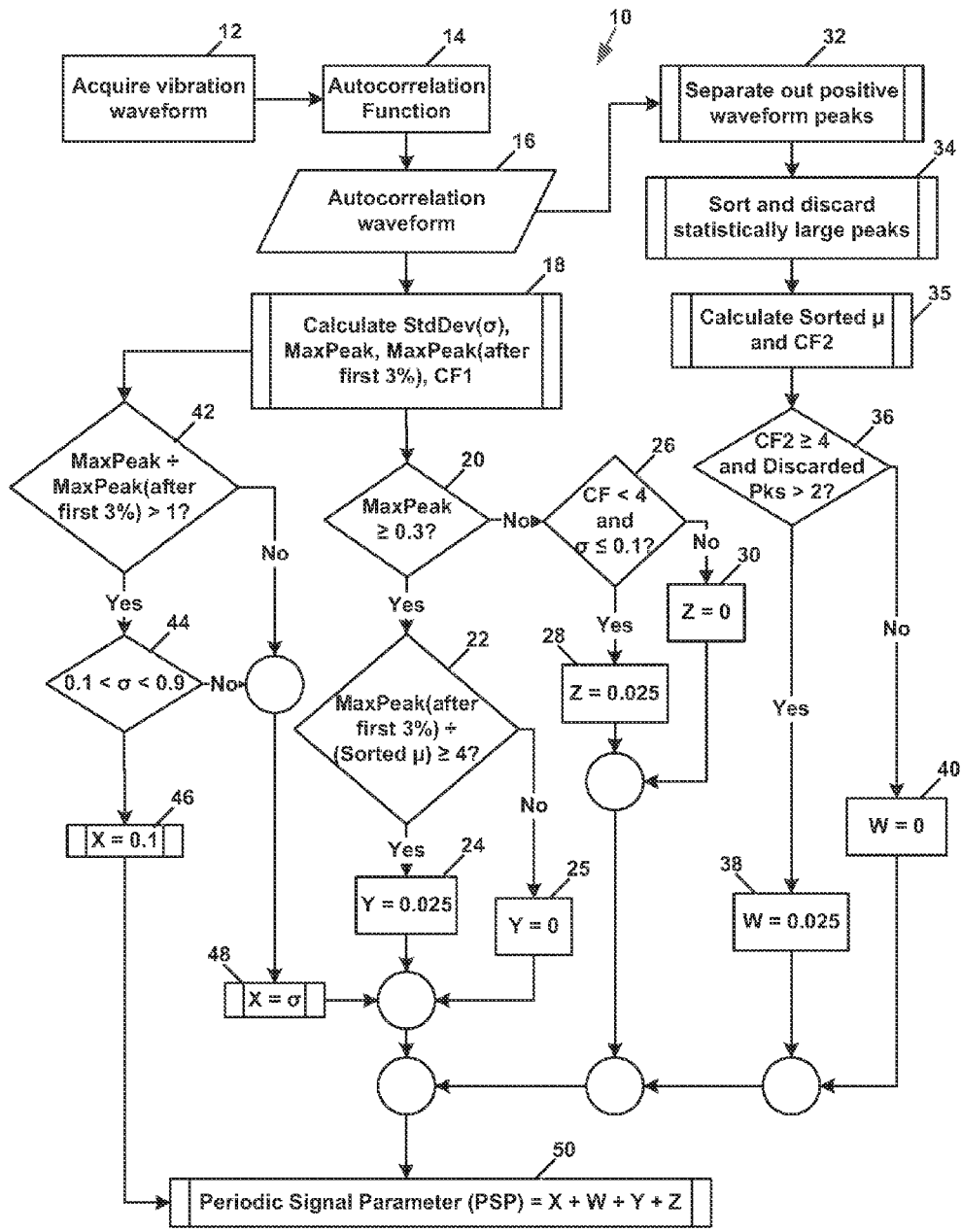
FIG. 2 depicts a flowchart of a method for determining a periodic signal parameter according to a preferred embodiment of the invention.

FIG. 2 depicts a flowchart of a method for calculating a periodic signal parameter (PSP) according to a preferred embodiment of the invention. A time-domain vibration waveform is measured, such as using the accelerometer 104 or other sensor attached to the machine 102 being monitored (step 12). An autocorrelation function is performed on the vibration waveform to determine how much of the energy in the waveform is periodic (step 14). In a preferred embodiment, the autocorrelation function cross-correlates the vibration waveform with itself to find repeating patterns within the waveform. The autocorrelation function outputs an autocorrelation waveform 16, examples of which are depicted in FIGS. 3-7. Several statistical characteristics of the autocorrelation waveform are calculated, including the standard deviation ($\sigma$), the maximum absolute peak amplitude in the waveform (MaxPeak), the maximum absolute peak after the first 3% of the waveform (MaxPeak (after first 3%)), and the crest factor (CF1) (step 18). The positive waveform peaks are sorted out (step 32), any of those peaks that are statistically too large are discarded (step 34), and the mean amplitude (sorted $\mu$) and the crest factor (CF2) of the remaining peaks are calculated (step 35). Methods for sorting and discarding peaks that are statistically too large are described hereinafter.

If MaxPeak is greater than or equal to 0.3 (step 20) and $$\frac{MaxPeak(\text{after first } 3\%)}{\text{sorted } \mu} \geq 4, \qquad (\text{step } 22)$$

then Y=0.025 (step 24). If MaxPeak is greater than or equal to 0.3 (step 20) and $$\frac{MaxPeak(\text{after first } 3\%)}{\text{sorted } \mu} < 4, \qquad (\text{step } 22)$$

then Y=0 (step 25).

If MaxPeak is less than 0.3 (step 20) and CF1 less than 4 and σ is less than or equal to 0.1 (step 26), then Z=0.025 (step 28). If MaxPeak is less than 0.3 (step 20) and CF1 is not less than 4 or a is greater than 0.1 (step 26), then Z=0 (step 30).

If CF2 is greater than or equal to 4 and the number of discarded peaks is greater than 2 (step 36), then W=0.025 (step 38). If CF2 is less than 4 or the number of discarded peaks is not greater than 2 (step 36), then W=0 (step 40).

If $$\frac{MaxPeak}{MaxPeak \text{ (after first 3\%)}} > 1 \qquad \text{(step 42)}$$

and σ is between 0.1 and 0.9 (step 44), then X=0.1 (step 46). If $$\frac{MaxPeak}{MaxPeak \text{ (after first 3\%)}} \leq 1 \qquad \text{(step 42)}$$

or σ is not between 0.1 and 0.9 (step 44), then X=σ (step 48).

The PSP is the sum of the values of X, W, Y and Z (step 50).

Figure 3:
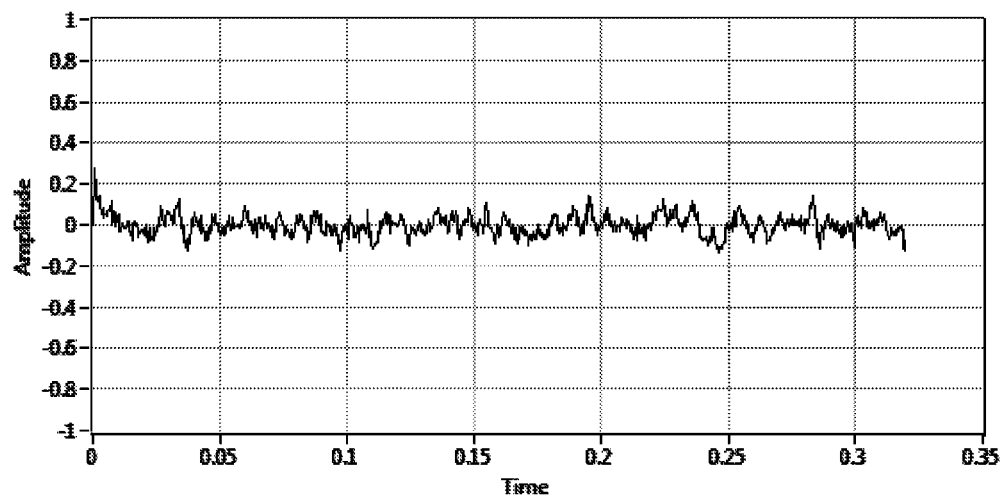
FIGS. 3-7 depict exemplary autocorrelated vibration waveforms for various values of a periodic signal parameter.
Figure 4:
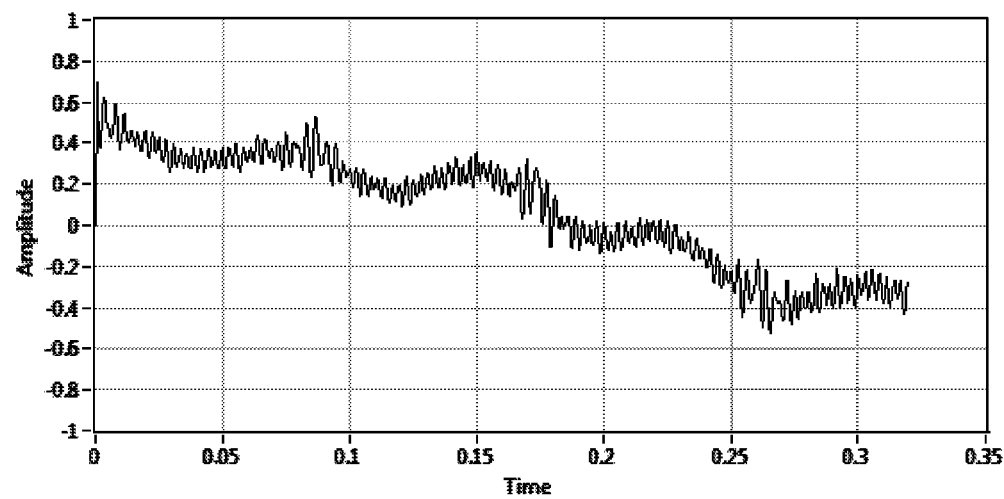
Figure 5:
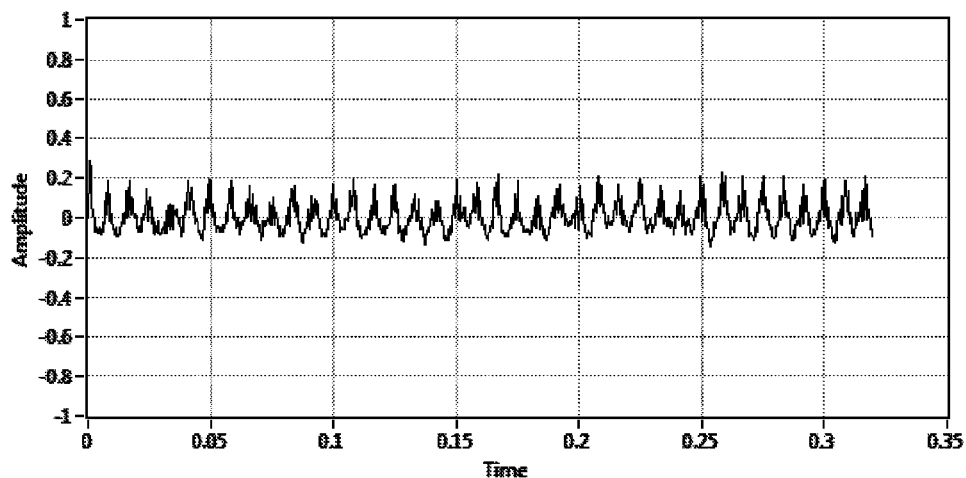
Figure 6:
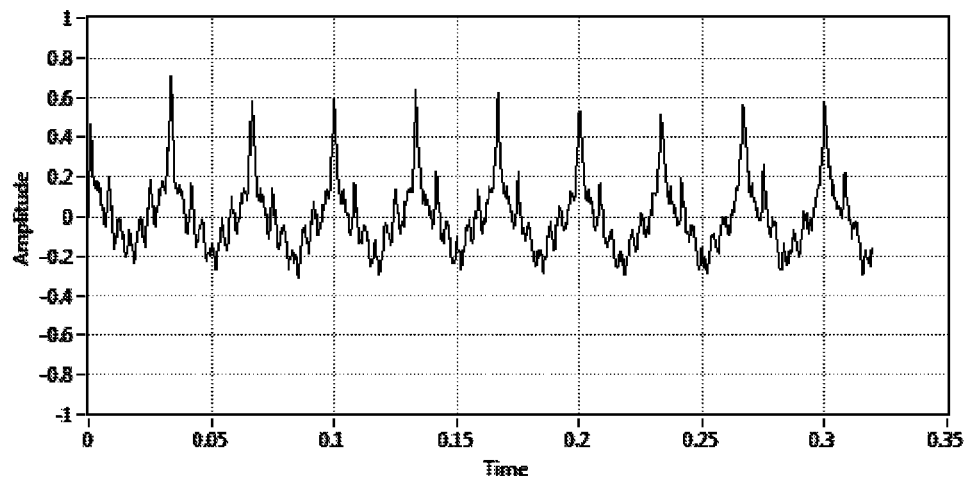
Figure 7:
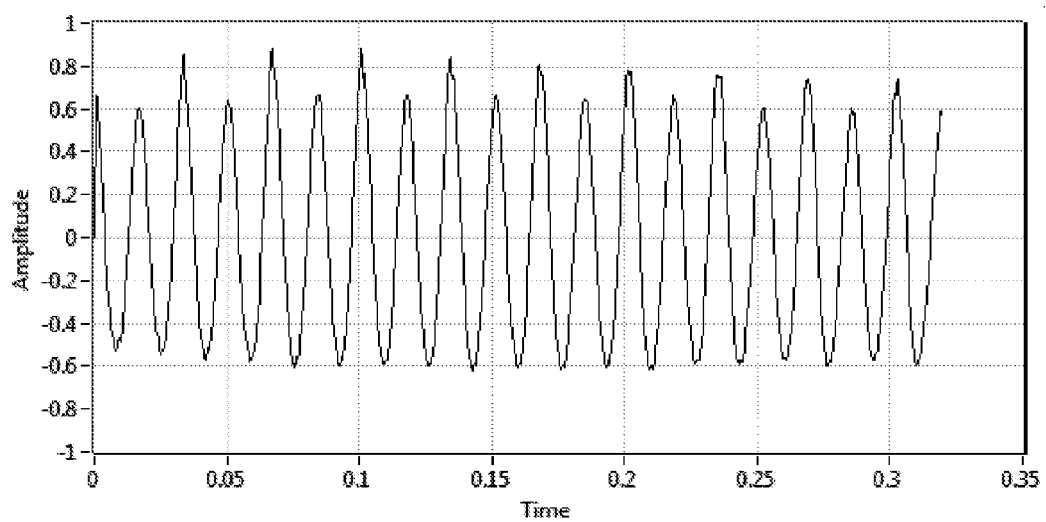

In general, smaller PSP values are indicative of more noise and less distinctive frequencies, while larger PSP values are symptomatic of more periodic (i.e. sinusoidal) signals relating to large single frequencies. As shown in FIG. 3, PSP values of less than a first threshold, such as 0.1, indicate that the vibration waveform is mostly noise. As shown in FIG. 4, the algorithm for the PSP assigns a value of 0.1 to signals having low amplitude, higher frequency data. This data may also prove to be bad data. As shown in FIG. 5, PSP values between first and second thresholds, such as between about 0.10 and 0.14, indicate that distinct frequencies are present but there is still a significant amount of random noise. As shown in FIG. 6, PSP values greater than the second threshold, such as greater than about 0.14, indicate very distinctive frequencies, such as vane pass or ball pass frequencies, along with small amplitude signals indicative of lower frequencies, such as RPM or cage along with their harmonics. As shown in FIG. 7, PSP values greater than a third threshold, such as greater than 0.5 and above, indicate large dominant single frequencies in the spectrum taken from the vibration waveform. The closer the PSP value is to 1.0, the waveform has more periodic (i.e. sinusoidal) signal components and less random noise.

Following are some advantages of generating a PSP.

The PSP provides a single number indicative of the periodic frequencies in a waveform.

Statistical values are calculated from the autocorrelated waveform and one or more of these values are combined to produce the PSP.

Indication of bad or noisy data is provided.

Information about periodicity can be extracted from a large data set and broadcast via a small bandwidth protocol such as HART, wireless HART, and other similar protocols.

The PSP value may be applied specifically to PeakVue™ data in order to distinguish between periodic and non-periodic faults, such as lubrication, cavitation, bearing, gear and rotor faults.

The PSP value can be used in conjunction with other information to generate an indication of machine condition (i.e. nature of mechanical fault, severity of the fault). The other information may include:
the original waveform;
processed versions of the waveform;
information (i.e. peak value, crest factor, kurtosis, skewness) obtained from the original vibration waveform;
information obtained from a processed version of the original waveform (i.e. PeakVue™ processed, rectified, or demodulated waveform); and/or
one or more rule sets.

A simple example is illustrated in Table 1 below, where derived values representing PSP output and Stress Wave Analysis output (for example, maximum peak in the PeakVue™ waveform or another derivative of PeakVue™ type analysis or another form of stress wave analysis) are used to distinguish between different types of faults. In the majority of cases, severity of the defect increases as the level of PeakVue™ impacting increases. Although the example below refers to a Stress Wave value, other embodiments may use other vibration waveform information indicative of an impacting or other fault condition.

TABLE 1

PSP and Stress Wave Analyses Outputs

| Periodic [right]<br>Stress Wave [below] | PSP - Low<br>(PSP < PSP threshold) | PSP - High<br>(PSP > PSP threshold) |
| --- | --- | --- |
| PeakVue ™ or other stress wave analysis - Low<br>(Stress Wave value <<br>Stress Wave threshold) | No fault indication:<br>no action called for<br>based on this finding | Early stage periodic fault related defect:<br>look for early indication of one of the<br>periodic fault types such as those listed<br>below |
| PeakVue ™ or other stress wave analysis - High<br>(Stress Wave value ><br>Stress Wave threshold) | Non-periodic fault:<br>look for further or<br>confirming evidence of<br>inadequate lubrication or<br>leak or contact friction or<br>pump cavitation | Periodic fault:<br>look for rolling element bearing defect or<br>gear defect or other source of repetitive<br>periodic mechanical impacting - use<br>frequency information and other information<br>to distinguish among multiple possible<br>causes |

A further embodiment of the present invention employs a programmable central processing unit programmed with program logic to assist a user with an interpretation of waveform information. The program logic compares the Periodic Signal Parameter and Stress Wave analysis information with expected or historical or empirically-derived experiential values to discern a relative ranking from low to high. Then discrete or graduated outputs, such as those portrayed in Table 1 above, are employed to select logically arrayed observations, findings, and recommendations. In addition to evaluating PSP and Stress Wave Analysis information, program logic sometimes prompts a user to supply additional information or obtains additional information from another source such as from a knowledge base, to enable the logic to distinguish between two or more possible logical results. For example, program logic that returns a high PSP and a high Stress Wave Analysis finding may select a rolling element defect finding rather than other possible findings within that category because a similarity is calculated when program logic compares a periodic frequency finding and a bearing fault frequency for a machine component identified in a knowledge base.

Another technique to differentiate between lubrication and pump cavitation is to look at the trend of the impacting. If it increases slowly, then insufficient lubrication should be suspected. If it increases suddenly on a pump, then it is likely pump cavitation. If combined with logic or inputs on a control system, then the logic could look for process configuration changes that occurred at the same time as the increase in impacting—along with a low PSP—to confirm pump cavitation. In some embodiments, the system suggests to the operator what action caused the cavitation, so that the operator can remove the cause and stop the machine from wearing excessively and failing prematurely.

Periodic Information Plot

Figure 8:
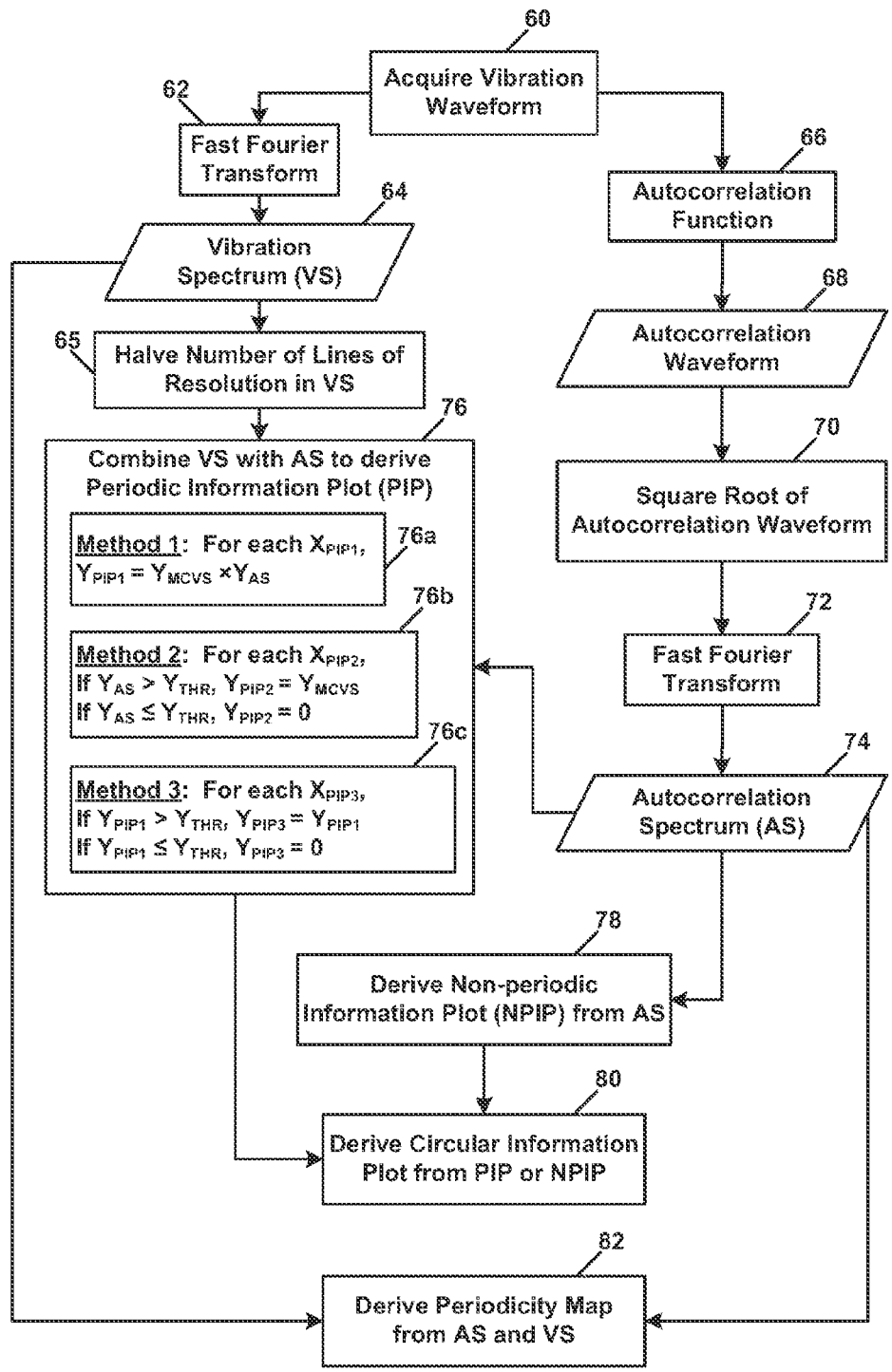
FIG. 8 depicts a flowchart of a method for generating a periodic information plot according to a preferred embodiment of the invention.

A preferred embodiment of the invention creates a new type of vibration spectrum, referred to herein as a Periodic Information Plot (PIP). In this embodiment, a signal is collected from plant equipment (i.e. rotating or reciprocating equipment) and is processed using two different sets of analysis techniques as depicted in FIG. 8.

Figure 9:
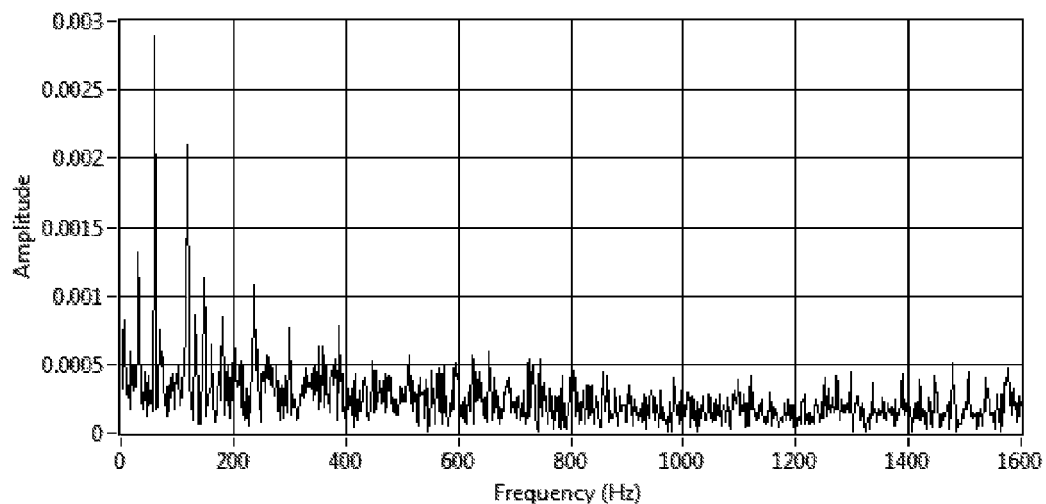
FIG. 9 depicts an exemplary standard vibration spectrum.

First, a waveform is acquired (step 60 of FIG. 8), such as a vibration waveform acquired using the system depicted in FIG. 1. If employing a high-pass filter and peak-hold decimation to an oversampled waveform to capture impacting information (such as using the PeakVue™ process), this may be a calculated waveform. An FFT of the waveform is taken (step 62), resulting in a vibration spectrum (VS) 64 with frequency on the X-axis and amplitude on the Y-axis, an example of which is shown in FIG. 9.

The waveform from step 60 is also autocorrelated (step 66) to generate a waveform referred to herein as the autocorrelation waveform 68, having time on the X-axis and the correlation factor on the Y-axis. The autocorrelation process accentuates periodic components of the original waveform, while diminishing the presence of random events in the original signal. As a result of the autocorrelation calculations, the associated waveform produced has half the x-axis (time) values as that of the original vibration waveform. Therefore, the timespan of the autocorrelation waveform will be half of that of the original vibration waveform. An optional step (70) takes the square root of the correlation factor (Y-axis values) to provide better differentiation between lower amplitude values.

Figure 10:
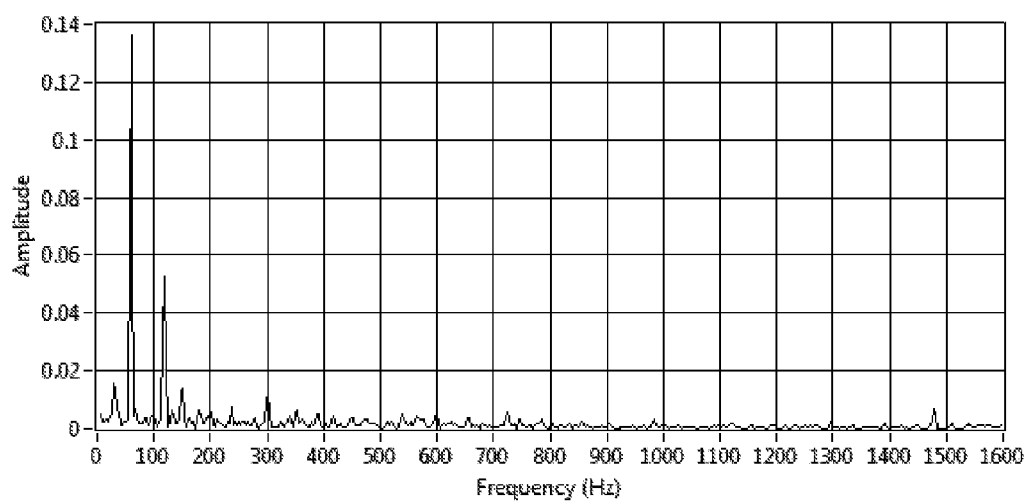
FIG. 10 depicts an exemplary autocorrelated vibration spectrum.

An FFT of the autocorrelation waveform is taken (step 72), resulting in an autocorrelation spectrum (AS) 74. Since random events have largely been removed from the autocorrelation waveform, the remaining signal in the autocorrelation spectrum is strongly related to periodic events. As shown in FIG. 10, the autocorrelation spectrum has frequency on the X-axis and amplitude related to the correlation factor on the Y-axis. Because the autocorrelation waveform's duration is half that of the vibration waveform, the associated autocorrelation spectrum has half the lines of resolution compared to the vibration spectrum.

In a preferred embodiment, the vibration spectrum and the autocorrelation spectrum are processed to derive a graph referred to herein as the Periodic Information Plot (PIP) (step 76). Several methods for processing the vibration spectrum and the autocorrelation spectrum may be used, three of which are described herein.

Because the vibration spectrum is twice the resolution of the autocorrelation spectrum, a point-to-point comparison for values on the x-axis (frequency) between the two spectra is not possible. However, a point-to-point comparison can be made by mathematically combining the amplitude values of two x-axis values in the vibration spectrum (step 65) for each associated x-axis value in the autocorrelation spectrum. Each $X_{AS}(n)$ value of the autocorrelation spectrum (where n=1 ... N, and N is the number of lines of resolution for the autocorrelation spectrum) is mapped to the $X_{VS}(2n)$ value on the vibration spectrum. The mathematically combined x-axis value is defined such that $X_{MCVS}(n)=X_{VS}(2n)$. The mathematically combined amplitude values $Y_{VS}(2n)$ and $Y_{VS}(2n-1)$ (herein termed $Y_{MCVS}(n)$) associated with the $X_{MCVS}(n)$ value from the vibration spectrum are calculated from the amplitudes of both the $X_{VS}(2n)$ and $X_{VS}(2n-1)$ frequencies from the x-axis. The calculation for deriving the mathematically combined amplitude value associated with the $X_{MCVS}(n)$ value from the vibration spectrum is:

$$Y_{MCVS}(n)=\sqrt{(Y_{VS}(2n-1))^2+(Y_{VS}(2n))^2}, \quad\quad \text{Eq. (0)}$$

where n=1 ... N and N is the number of lines of resolution found in the autocorrelation spectrum.

Figure 11:
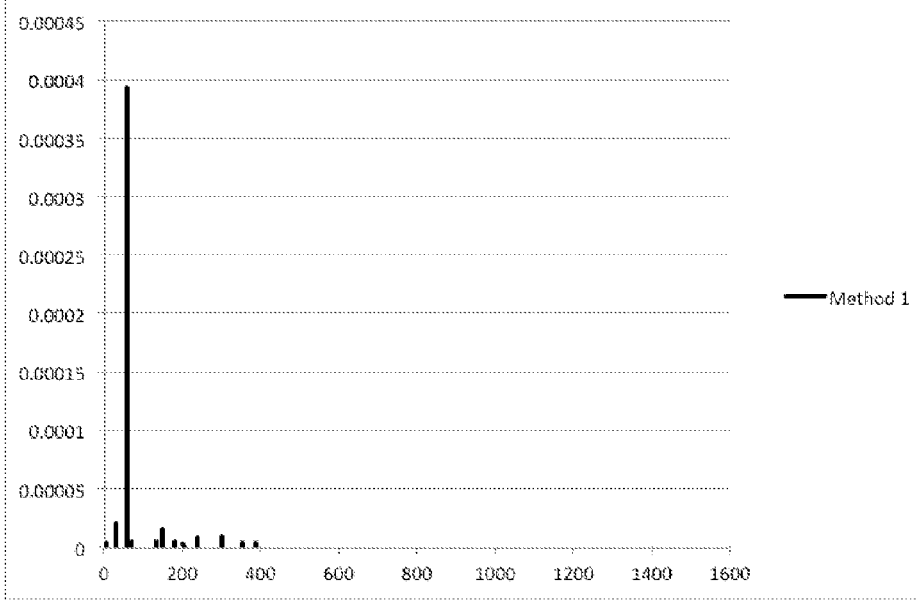
FIGS. 11-17 depict periodic information plots generated according to preferred embodiments of the invention.

In a first method (step 76a), for each X-value in the PIP ($X_{PIP1}$), the Y-value in the PIP ($Y_{PIP1}$) is determined by multiplying the mathematically combined Y-value in the vibration spectrum ($Y_{MCVS}$) by the corresponding Y-value in the autocorrelation spectrum ($Y_{AS}$), according to:

$$Y_{PIP1}(n)=Y_{MCVS}(n)\times Y_{AS}(n) \quad\quad \text{Eq. (1)}$$

for n=1 to N, where N is the number of X-values (frequency values) in the autocorrelation spectrum. Since amplitudes of periodic signals in the autocorrelation spectrum are higher than the amplitudes of random signals, the multiplication process will accentuate the periodic peaks while decreasing non-periodic peaks. An example of a PIP formed by the first method is depicted in FIG. 11. In all of the examples depicted herein, N=1600.

In a second method (step 76b), for each X-value in the PIP ($X_{PIP2}$), the Y-value in the PIP ($Y_{PIP2}$) is determined by comparing the corresponding Y-value in the autocorrelation spectrum ($Y_{AS}$) to a predetermined threshold value ($Y_{THR}$). For each autocorrelation spectrum amplitude greater than this threshold value, the associated amplitude for PIP ($Y_{PIP2}(n)$) will be set to the corresponding mathematically combined value from the vibration spectrum ($Y_{MCVS}(n)$). $Y_{AS}$ values above the predetermined threshold indicate data that is largely periodic. Thus, the $Y_{PIP2}$ values are determined according to:

$$\text{If } Y_{AS}(n)>Y_{THR}, Y_{PIP2}(n)=Y_{MCVS}(n) \quad\quad \text{Eq. (2a)}$$

$$\text{If } Y_{AS}(n)\leq Y_{THR}, Y_{PIP2}(n)=0 \text{ (or some other default level)} \quad\quad \text{Eq. (2b)}$$

for n=1 to N.

Figure 12:
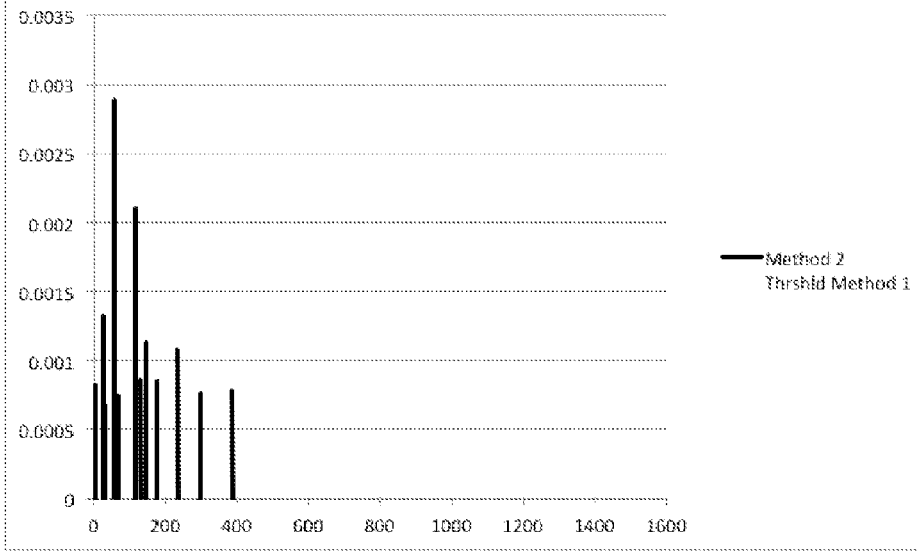

In one preferred embodiment of the second method, $Y_{THR}$ is set to only include a percentage of the largest peaks from the autocorrelation spectrum. The percentage may be calculated based on the percent periodic signal in the autocorrelation waveform. The percent periodic signal is calculated based on the autocorrelation coefficient, which is the square root of the Y-value of the largest peak in the autocorrelation waveform. For this method, only the percent periodic signal of the total number of autocorrelation spectrum peaks will be evaluated. An example of a PIP formed by this method, with $Y_{THR}$ set to 59%, is depicted in FIG. 12.

Figure 13:
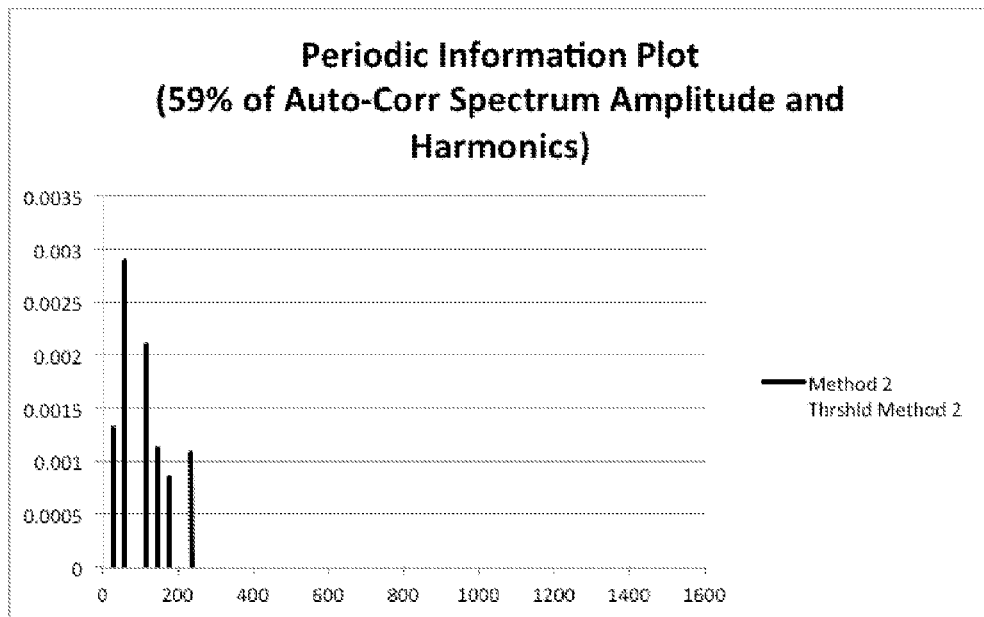

In another preferred embodiment of the second method, $Y_{THR}$ is set to include only peaks with values that are within the "percent periodic signal" of the largest peak value in the autocorrelation spectrum. These peaks, along with their harmonics that appear in the autocorrelation spectrum, will be utilized as the group of peaks to be intersected with those in the vibration spectrum to form the PIP. An example of a PIP formed by this method, with $Y_{THR}$ set to 59%, is depicted in FIG. 13.

Figure 14:
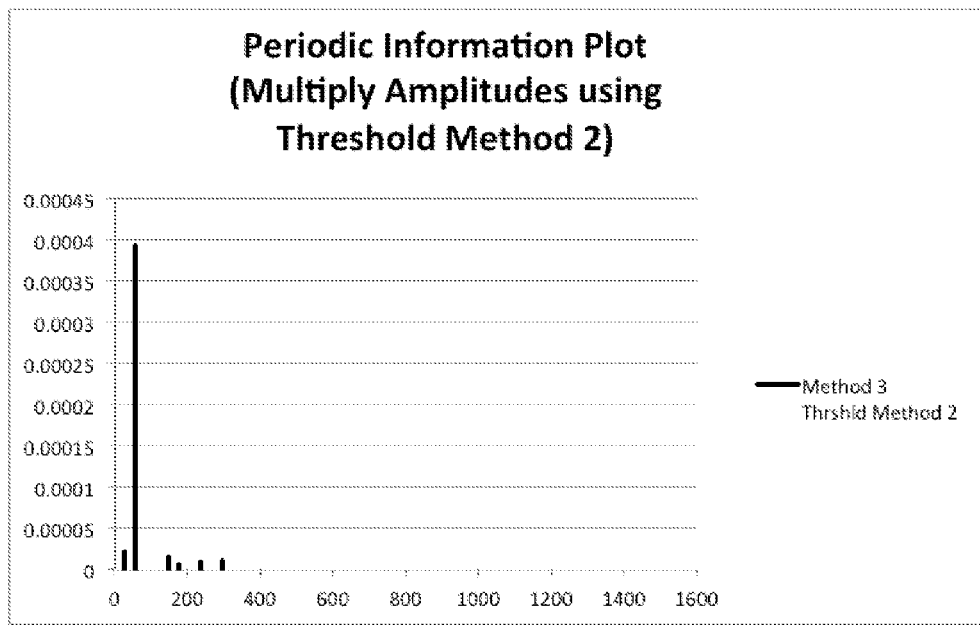

In a third method (step 76*c*), the PIP is determined according to the first method described above, and then the threshold of the second method is applied to the PIP according to:

$$\text{If } Y_{PIP1}(n) > Y_{THR}, Y_{PIP3}(n) = Y_{PIP1}(n) \quad \text{Eq. (3a)}$$

$$\text{If } Y_{PIP1}(n) \le Y_{THR}, Y_{PIP3}(n) = 0 \text{ (or some other default level)} \quad \text{Eq. (3b)}$$

for n=1 to N. An example of a PIP formed by this method is depicted in FIG. 14.

Figure 15:
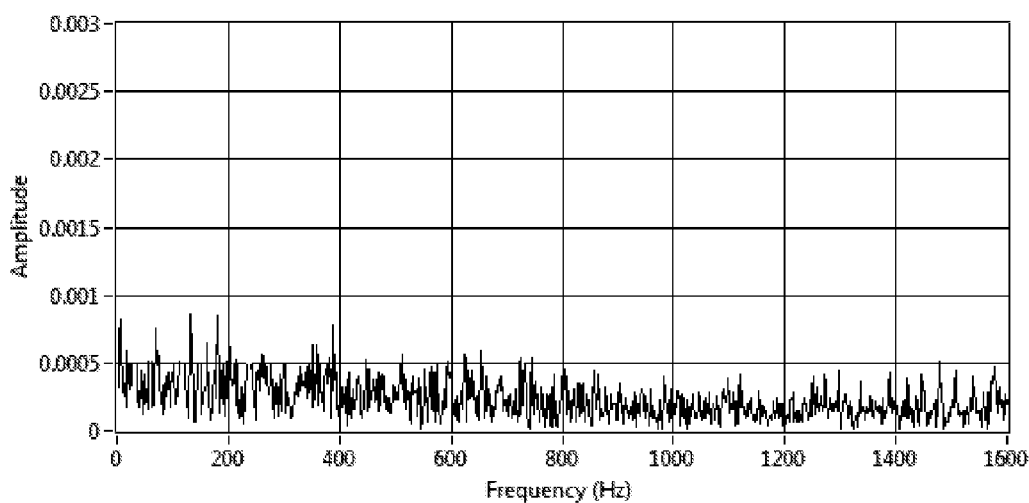

Some embodiments also derive a Non-periodic Information Plot (NPIP) that consists of only the Y-values of the autocorrelation spectrum that are less than a predetermined threshold (step 78). Thus, the NPIP includes only non-periodic components. An example of an NPIP formed by this method is depicted in FIG. 15.

Figure 16:
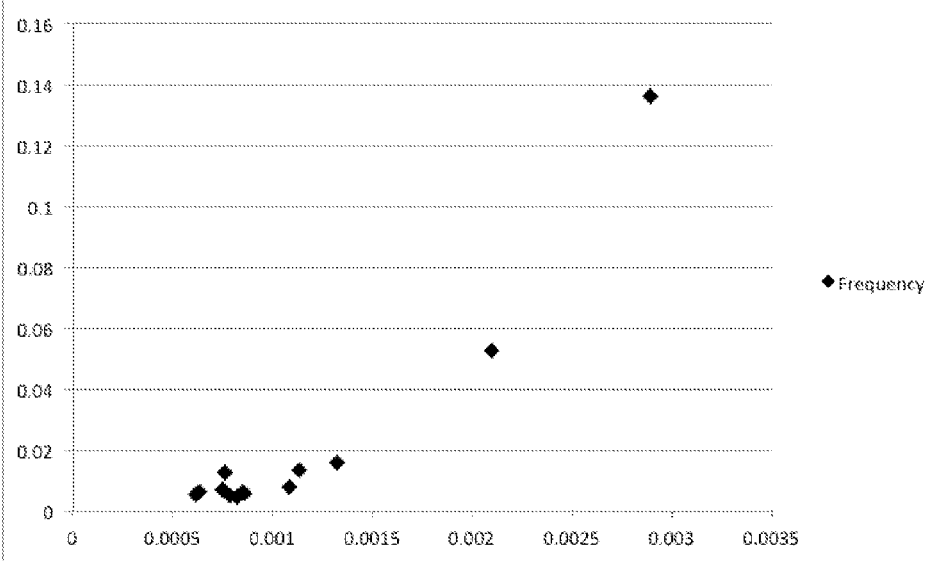

Some embodiments also derive a Periodicity Map from the vibration spectrum and the autocorrelation spectrum (step 82). The Periodicity Map is created by pairing the mathematically combined Y-values from the vibration spectrum and the autocorrelation spectrum corresponding to any given X-value of the autocorrelation spectrum. These pairs are plotted with the mathematically combined Y-value from the vibration spectrum $Y_{MCVS}(n)$ as the X-value of the point on the map $X_{PM}(n)$, and the Y-value from the autocorrelation spectrum $Y_{AS}(n)$ as the corresponding Y-value on the map $Y_{PM}(n)$, according to:

$$X_{PM}(n) = Y_{MCVS}(n) \quad \text{Eq. (4a)}$$

$$Y_{PM}(n) = Y_{AS}(n) \quad \text{Eq. (4b)}$$

for n=1 to N. As shown in FIG. 16, the resulting graph resembles a probability mapping. A specific software implementation would allow the user to run a cursor over each point to view the values creating that point.

Figure 17:
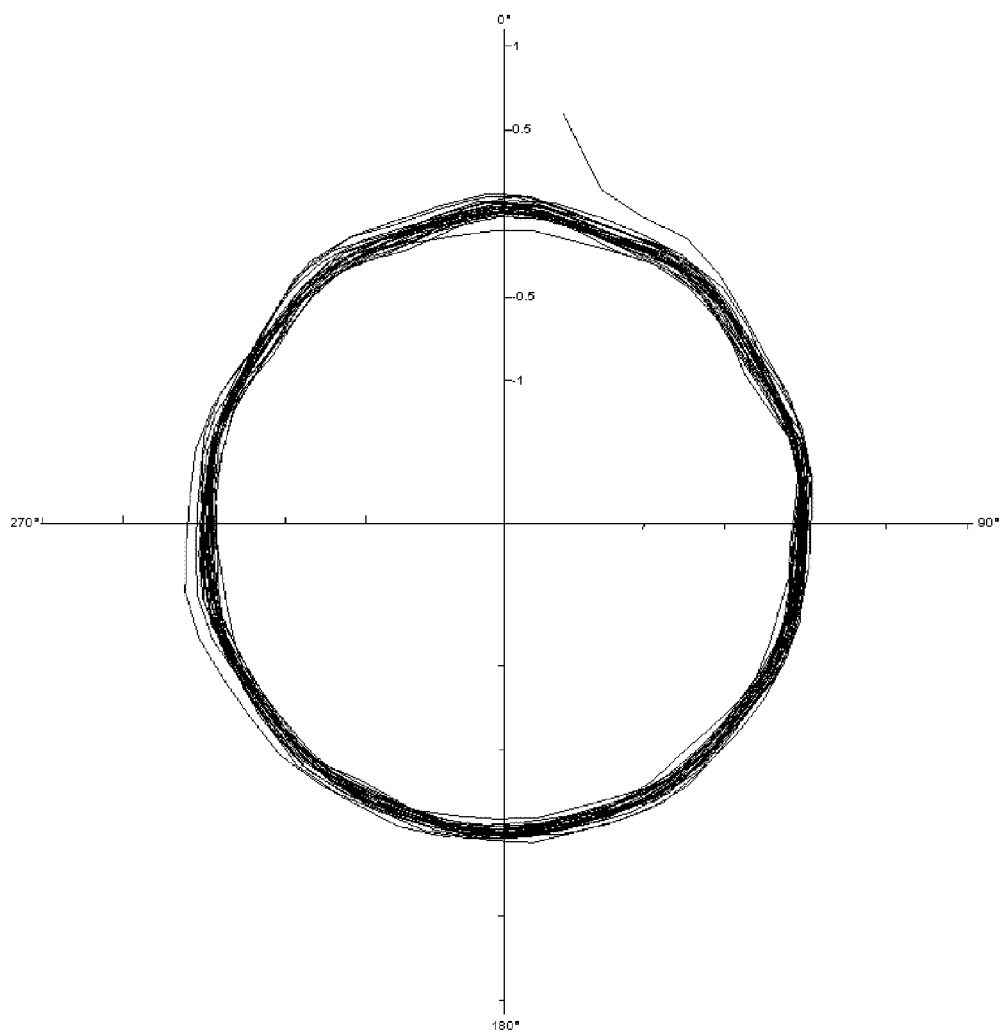

Some embodiments also derive a Circular Information Plot from any of the Periodic Information Plots described above (step 80). Once a linear PIP is calculated, an inverse FFT can be applied to generate an "information waveform." A Circular Information Plot can then be generated from this information waveform. An example of a Circular Information Plot formed by this method is depicted in FIG. 17.

Although preferred embodiments of the invention operate on vibration signals, the invention is not limited to only vibration signals. Periodic Signal Parameters and Periodic Information Plots may be derived from any signal containing periodic components.

Methods for Sorting and Discarding Statistically Outlying Peaks in the Autocorrelation Waveform (Step 34 in FIG. 2).

The following routine takes an array of data values, such as values of positive peaks in the autocorrelation waveform, and discards values outside the statistically calculated boundaries. In a preferred embodiment, there are four methods or criteria for setting the boundaries.

Method 1: Non-Conservative, Using Minimum and Maximum Statistical Boundaries

Consider an array of P values (or elements) where $P_0$ represents the number of values in the present array under evaluation. Now let $P_{-1}$ represent the number of values in the array evaluated a single step before $P_0$, let $P_{-2}$ represent the number of values in the array evaluated a single step before $P_{-1}$, and let $P_{-3}$ represent the number of values in the array evaluated a single step before $P_{-2}$.

Step 1:

While evaluating the array of values for either the first time or $P_0 \ne P_{-1}$,
{
  Calculate the mean ($\mu$) and standard deviation ( ) for $P_0$ If $\dfrac{n\sigma}{\mu} \ge x$, where $x = 0.1$ and $n = 1$, 2 or 3 in the preferred embodiment, then Include array values such that
  $\mu - n$ < values < $\mu + n$
  Else
    STOP, values are within statistical boundaries.
  Endif
}

Step 2:

If $P_0 = P_{-1}$, then
  While $P_{-1} \ne P_{-2}$, and $P_0 = P_{-1}$
  {
    Calculate the mean ($\mu$) and standard deviation ( ) for $P_0$ If $\dfrac{n\sigma}{2\mu} \ge x$, where $x = 0.1$ and $n = 1$, 2 or 3 in the preferred embodiment, then Include array values such that
    $\mu - \dfrac{n\sigma}{2}$ < values < $\mu + \dfrac{n\sigma}{2}$
    Else
      STOP, values are within statistical boundaries.
    Endif
  }
Endif Step 3:

If $P_0 = P_{-1} = P_{-2}$, and $P_{-2} \ne P_{-3}$, then
  Calculate the mean ($\mu$) and standard deviation ($\sigma$) for $P_0$
  Include array values such that
  $0.9\mu$ < values < $1.1\mu$
Else
  STOP, values are within statistical boundaries.
Endif Method 2: Non-Conservative, Using Maximum Statistical Boundary Only (No Minimum Boundary)

Use the same procedure as in Method 1 except only values exceeding the upper statistical boundaries are discarded. The minimum boundary is set to zero.

Method 3: Conservative, Using Minimum and Maximum Statistical Boundaries

Discard values based on Method 1, Step 1 only.

Method 4: Conservative, Using Maximum Statistical Boundary Only (No Minimum Boundary)

Discard values based on Method 1, Step 1 only and based on values exceeding the upper statistical boundaries. The minimum boundary is set to zero.

Example of Method 1 for Sorting Out Statistical Outliers

As an example of the sorting Method 1, consider an original set of values, $P_0$, containing the 21 values listed below in Table 2 below, with n=1.

TABLE 2

| |
|---|
| 0.953709 |
| 0.828080 |
| 0.716699 |
| 0.653514 |
| 0.612785 |
| 0.582031 |
| 0.579209 |
| 0.557367 |
| 0.545801 |
| 0.495215 |
| 0.486426 |
| 0.486053 |
| 0.475123 |
| 0.472348 |
| 0.467129 |
| 0.465488 |
| 0.446327 |
| 0.440497 |
| 0.437959 |
| 0.427256 |
| 0.411627 |

The mean ($\mu$) of this original set, $P_0$, is 0.54955 and standard deviation ($\sigma$) is 0.13982. Therefore, in Step 1 of Method 1, $$\frac{n\sigma}{\mu} = 1 * \frac{0.13982}{0.54955} = 0.25442.$$

Since 0.25442 is greater than 0.1, calculate $$\mu - n\sigma = 0.54955 - 1*0.13982 = 0.409735$$

and $$\mu + n\sigma = 0.54955 + 1*0.13982 = 0.689373.$$

Next, define the set $P_{-1}=P_0$ and define a new set $P_0$, the values of which are all the values of $P_{-1}$ that are between the values $\mu+\sigma=0.689343$ and $\mu-\sigma=0.409735$. The set $P_0$ now contains the values listed below in Table 3, wherein three outlier values have been eliminated.

TABLE 3

| |
|---|
| 0.653514 |
| 0.612785 |
| 0.582031 |
| 0.579209 |
| 0.557367 |
| 0.545801 |
| 0.495215 |
| 0.486426 |
| 0.486053 |
| 0.475123 |
| 0.472348 |
| 0.467129 |
| 0.465488 |
| 0.446327 |
| 0.440497 |
| 0.437959 |
| 0.427256 |
| 0.411627 |

Since $P_0 \neq P_{-1}$, Step 1 is repeated, where for the set $P_0$:

$\mu=0.50234$, $\sigma=0.06946$, $\sigma/\mu=0.138263$, $\mu+\sigma=0.571797$, and $\mu-\sigma=0.432887$.

Now define the set $P_{-2}=P_{-1}$, and $P_{-1}=P_0$ and define a new set $P_0$, the values of which are all the values of $P_{-1}$ that are between the values $\mu+\sigma=0.571797$ and $\mu-\sigma=0.432887$. The set $P_0$ now contains the values listed below in Table 4, wherein four more outlier values have been eliminated.

TABLE 4

| |
|---|
| 0.557367 |
| 0.545801 |
| 0.495215 |
| 0.486426 |
| 0.486053 |
| 0.475123 |
| 0.472348 |
| 0.467129 |
| 0.465488 |
| 0.446327 |
| 0.440497 |
| 0.437959 |

Since $P_0 \neq P_{-1}$, Step 1 is repeated, where for the set $P_0$:

$\mu=0.481311$, $\sigma=0.037568$, and $\sigma/\mu=0.078053$.

Since $\sigma/\mu=0.078053 \leq 0.1$, all the members of the array $P_0$ are statistically close in value and need no more sorting.

If at any point in the calculations $P_0=P_{-1}$ and $P_{-1} \neq P_{-2}$, then Step 2 would be executed instead of Step 1. In the example above, since $P_0 \neq P_{-1}$ for every iteration, only Step 1 was necessary for the calculations.

The foregoing description of preferred embodiments for this invention has been presented for purposes of illustration and description. They are not intended to be exhaustive or to limit the invention to the precise form disclosed. Obvious modifications or variations are possible in light of the above teachings. The embodiments are chosen and described in an effort to provide the best illustrations of the principles of the invention and its practical application, and to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. A method for analyzing periodic information in a signal associated with a machine or process, the method comprising:
    (a) acquiring the signal over a time period using a sensor associated with the machine or process;
    (b) generating an autocorrelation waveform based on the signal;
    (c) determining a periodic signal parameter value based at least in part on the autocorrelation waveform, the periodic signal parameter value comprising a single real number indicative of a level of periodic information in the signal;

(d) determining a vibration waveform value based on the signal;

(e) comparing the vibration waveform value to a vibration waveform value threshold;

(f) comparing the periodic signal parameter value to a periodic signal parameter value threshold; and (g) generating an output indicating a no-fault condition of the machine or process if the vibration waveform value is less than the vibration waveform value threshold and the periodic signal parameter value is less than the periodic signal parameter value threshold.

2. The method of claim 1 wherein step (c) comprises determining the periodic signal parameter value based at least in part on a combination of statistical values calculated from the autocorrelation waveform.

3. The method of claim 2 wherein step (c) comprises:
(c1) determining a standard deviation of the autocorrelation waveform;
(c2) determining a maximum absolute peak amplitude over all of the time period of the autocorrelation waveform;
(c3) determining a maximum absolute peak amplitude after the first three percent of the time period of the autocorrelation waveform;
(c4) determining a crest factor of the autocorrelation waveform; and
(c5) determining the periodic signal parameter value based at least in part on the standard deviation, the maximum absolute peak amplitude over all of the time period of the autocorrelation waveform, the maximum absolute peak amplitude after the first three percent of the time period of the autocorrelation waveform, and the crest factor.

4. The method of claim 3 wherein the periodic signal parameter value comprises a sum of at least a first portion, a second portion and a third portion.

5. The method of claim 4 wherein step (c) further comprises determining the first portion of the periodic signal parameter value by:
(c6) setting the first portion equal to the standard deviation of the autocorrelation waveform if a dividend of the maximum absolute peak amplitude over all of the time period of the autocorrelation waveform divided by the maximum absolute peak amplitude after the first three percent of the time period of the autocorrelation waveform is not greater than one; and
(c7) setting the first portion equal to 0.1 if the dividend of the maximum absolute peak amplitude over all of the time period of the autocorrelation waveform divided by the maximum absolute peak amplitude after the first three percent of the time period of the autocorrelation waveform is greater than one, and the standard deviation of the autocorrelation waveform is greater than 0.1 and less than 0.9.

6. The method of claim 4 wherein step (c) further comprises determining the second portion of the periodic signal parameter value by:
(c6) determining whether the maximum absolute peak amplitude over all of the time period of the autocorrelation waveform is greater than or equal to 0.3;
(c7) determining whether a dividend of the maximum absolute peak amplitude after the first three percent of the time period of the autocorrelation waveform divided by a mean amplitude of the autocorrelation waveform is greater than or equal to 4;
(c8) setting the second portion equal to 0.025 if the maximum absolute peak amplitude over all of the time period of the autocorrelation waveform is greater than or equal to 0.3, and the dividend of the maximum absolute peak amplitude after the first three percent of the time period of the autocorrelation waveform divided by a mean amplitude of the autocorrelation waveform is greater than or equal to 4;
(c9) setting the second portion equal to 0 if the maximum absolute peak amplitude over all of the time period of the autocorrelation waveform is greater than or equal to 0.3, and the dividend of the maximum absolute peak amplitude after the first three percent of the time period of the autocorrelation waveform divided by a mean amplitude of the autocorrelation waveform is not greater than or equal to 4;
(c10) setting the second portion equal to 0.025 if the maximum absolute peak amplitude in all of the time period of the autocorrelation waveform is not greater than or equal to 0.3, and the crest factor of the autocorrelation waveform is less than 4 and the standard deviation of the autocorrelation waveform is less than or equal to 0.1; and
(c11) setting the second portion equal to 0 if the maximum absolute peak amplitude in all of the time period of the autocorrelation waveform is not greater than or equal to 0.3, and the crest factor of the autocorrelation waveform is not less than 4 or the standard deviation of the autocorrelation waveform is not less than or equal to 0.1.

7. The method of claim 4 wherein step (c) further comprises determining the third portion of the periodic signal parameter value by:
(c6) discarding negative peaks in the autocorrelation waveform;
(c7) of peaks remaining after step (c6), discarding peaks in the autocorrelation waveform that are outside a statistical range;
(c8) determining a mean value of peaks in the autocorrelation waveform remaining after step (c7);
(c9) determining a crest factor of the peaks in the autocorrelation waveform remaining after step (c7);
(c10) setting the third portion to 0.025 if the crest factor determined in step (c9) is greater than or equal to 4, and the number of peaks discarded in step (c7) is greater than 2; and
(c11) setting the third portion to 0 if the crest factor determined in step (c9) is not greater than or equal to 4, or the number of peaks discarded in step (c7) is not greater than 2.

8. The method of claim 1 further comprising:
(h) generating an output indicating an early-stage periodic defect condition of the machine or process if the vibration waveform value is less than the vibration waveform value threshold and the periodic signal parameter value is greater than the periodic signal parameter value threshold;
(i) generating an output indicating a non-periodic fault condition of the machine or process if the vibration waveform value is greater than the vibration waveform value threshold and the periodic signal parameter value is less than the periodic signal parameter value threshold; and
(j) generating an output indicating a periodic fault condition of the machine or process if the vibration waveform value is greater than the vibration waveform value threshold and the periodic signal parameter value is greater than the periodic signal parameter value threshold.

9. The method of claim 1 further comprising:
(h) determining that the signal comprises random noise, that bad data has been collected, or that data was collected for too short a time to indicate fault-related frequencies, if the periodic signal parameter value is less than or equal to a first threshold value;
(i) determining that the signal comprises distinct frequencies with less noise than in step (d) if the periodic signal parameter value is greater than the first threshold value and less than or equal to a second threshold value;
(j) determining that the signal comprises dominate single frequencies with less noise than in step (e) if the periodic signal parameter value is greater than the second threshold value.

\* \* \* \* \*